United States Patent [19]

Shalmi et al.

[11] Patent Number: 5,726,202
[45] Date of Patent: Mar. 10, 1998

[54] BENIGN PROSTATIC HYPERTROPHY

[75] Inventors: Michael Shalmi; Niels Dyhr Christensen, both of København; Niels Korsgaard, Værløse; Birgitte Hjort Guldhammer, Hillerød, all of Denmark

[73] Assignee: Novo Nordisk A/S, Bagsvaerd, Denmark

[21] Appl. No.: 678,275

[22] Filed: Jul. 11, 1996

[51] Int. Cl.$^6$ .......................... A61K 31/40; A61K 31/35
[52] U.S. Cl. .............................. 514/422; 514/456
[58] Field of Search ........................ 514/422, 456

[56] References Cited

U.S. PATENT DOCUMENTS 4,310,523  1/1982  Neumann ............................ 424/240

OTHER PUBLICATIONS

Dhar, J.D. et al., Andrologia, vol. 15, No. 5, pp. 463–467, (1983).

Primary Examiner—Kimberly Jordan
Attorney, Agent, or Firm—Steve T. Zelson; Cheryl H. Agris

[57] ABSTRACT

The present invention provides novel uses of compounds of general formula I

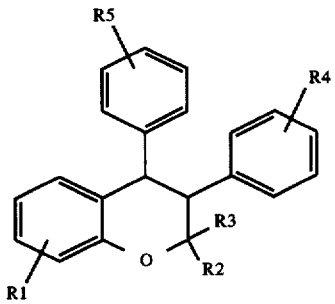

wherein $R^1$, $R^4$ and $R^5$ are individually hydrogen, hydroxy, halogen, trifluoromethyl, lower alkyl, lower alkoxy or (tertiary amino) (lower alkoxy); and $R^2$ and $R^3$ are individually hydrogen or lower alkyl, or as a pharmaceutically acceptable salt thereof in combination with a pharmaceutically acceptable carrier for the manufacture of a pharmaceutical composition for the treatment or prophylaxis of benign prostatic hypertrophy

18 Claims, No Drawings

BENIGN PROSTATIC HYPERTROPHY

Use of 3,4-diphenyl chromans for the manufacture of a pharmaceutical composition for the treatment or prophylaxis of benign prostatic hypertrophy This application claims priority under 35 U.S.C. §119(e) of provisional application 60/009,905, filed Jan. 11, 1996, the contents of which are incorporated herein by reference.

FIELD OF THIS INVENTION

The present invention relates to the use of compounds of the general formula I for the treatment of patients suffering from benign prostatic hypertrophy and prophylaxis hereof. The present invention also embraces pharmaceutical compositions comprising these compounds and methods of using the compounds and their pharmaceutical compositions.

BACKGROUND OF THIS INVENTION

Benign prostatic hypertrophy is an almost universal phenomenon in aging men. It refers to a nodular enlargement of the gland due to hyperplasia of both glandular and stromal components. The incidence of this disease is only 8% during the fourth decade, but it reaches 50% in the fifth decade and 75% in the eighth decade. The disorder is not a major cause of death, but it is a leading cause of morbidity in elderly men. The pathogenesis is not well-understood, but dihydrotestosterone together with increasing levels of estrogen which occur in men act synergistically to induce prostatic growth. The treatment is surgical, which, however, can only be offered to a small selected number of patients with this disease because the majority of men above age 60 have some degree of prostatic hyperplasia. No protecting factors other than castration have been identified and no effective pharmacological treatment or profylaxis exists.

Centchroman is a non-steroidal compound known to have antiestrogenic activity. It is in use in India as an oral contraceptive (see, for example, Salman et al., U.S. Pat. No. 4,447,622; Singh et al., Acta Endocrinal (Copenh) 126 (1992), 444–450; Grubb, Curr Opin Obstet Gynecol 3 (1991), 491–495; Sankaran et al., Contraception 9 (1974), 279–289; Indian Patent Specification No. 129187). Centchroman has also been investigated as an anti-cancer agent for treatment of advanced breast cancer (Misra et al., Int J Cancer 43 (1989), 781–783. Recently, centchroman as a racemate has been found as a potent cholesterol lowering pharmaceutical expressed by a significant decrease of the serum concentrations (S. D. Bain et al., J Min Bon Res 9 (1994), S 394).

U.S. Pat. No. 5,453,442 describes methods of lowering serum cholesterol and inhibiting smoother muscle cell proliferation in humans and inhibiting uterine fibroid disease and endometriosis in women by administering compounds of formula I as shown therein. Furthermore, U.S. Pat. No. 5,280,040 describes methods and pharmaceutical compositions for reducing bone loss using 3,4-diaryl chromans and their pharmaceutically acceptable salts. There is no disclosure in the patents of using the compounds to treat or prevent benign prostatic hypertrophy.

One object of the present invention is to provide compounds which can effectively be used in the treatment or prophylaxis of benign prostatic hypertrophy.

BRIEF DESCRIPTION OF THIS INVENTION

It has, surprisingly, been found that compounds of the general formula I as stated in claim 1 can be used in the treatment or prophylaxis of benign prostatic hypertrophy.

DETAILED DESCRIPTION OF THIS INVENTION

The present invention is based in part on the discovery that a representative 3,4-diarylchroman, centchroman (3,4-trans-2,2-dimethyl-3-phenyl-4-[p-(beta-pyrrolidinoethoxy)phenyl]-7-methoxychroman) is effective against benign prostatic hypertrophy, inter alia in rats. An increased prostate weight is the cardinal observation seen in patients with prostatic hypertrophy, hence these data thus indicate that the 3,4-diarylchromans are useful as therapeutic agents against benign prostatic hypertrophy in mammals, including primates such as humans.

Within the present invention, compounds of formula I as stated in claim 1 are used for benign prostatic hypertrophy in a patient. Within formula I, $R^1$, $R^4$ and $R^5$ are individually hydrogen, hydroxy, halogen, trifluoromethyl, lower alkyl, lower alkoxy or (tertiary amino)(lower alkoxy); and $R^2$ and $R^3$ are individually hydrogen or a lower alkyl. As used herein, the term "lower alkyl" includes straight and branched chain alkyl radicals containing from 1 to 6 carbon atoms, such as methyl, ethyl, n-propyl, isopropyl, n-butyl, tert-butyl, n-amyl, sec-amyl, n-hexyl, 2-ethylbutyl, 2,3-dimethylbutyl and the like. The term "lower alkoxy" includes straight and branched chain alkoxy radicals containing from 1 to 6 carbon atoms, such as methoxy, ethoxy, n-propoxy, isopropoxy, n-butoxy, tert-butoxy, n-amyloxy, sec-amyloxy, n-hexyloxy, 2-ethylbutoxy, 2,3-dimethylbutoxy and the like. "Halogen" includes chloro, fluoro, bromo and iodo. Herein, the term "(tertiary amino)(lower alkoxy)" is a lower alkoxy group which is substituted by a tertiary amino radical. The tertiary amino radical may be a N,N-dialkylamine such as a N,N-dimethylamino, N,N-diethylamino, N,N-dipropylamino and N,N-dibutylamino or a polymethyleneimine, e.g., piperidine, pyrrolidine, N-methylpiperazine or morpholine. Preferred compounds include those in which $R^1$ is lower alkoxy; $R^2$ and $R^3$ are lower alkyl, especially methyl; $R^4$ is hydrogen; and $R^5$ is (tertiary amino)(lower alkoxy) of the polymethyleneimine type. Within particularly preferred embodiments, $R^1$ is in the 7-position and is lower alkoxy, particularly methoxy; each of $R^2$ and $R^3$ is methyl, $R^4$ is hydrogen, and $R^5$ is in the 4-position and is a (tertiary amino)(lower alkoxy) radical such as 2-(pyrrolidin-1-yl)ethoxy. To be included by this invention are all pharmaceutically acceptable salts of the mentioned compounds of formula I.

It is preferred to use the compounds of formula I in the transconfiguration. These compounds may be used as racemic mixtures, or the isolated d- or l- enantiomers may be used. The trans-l-enantiomers are more preferred.

A particularly preferred compound for use within the present invention is centchroman having the formula IV as stated in claim 11.

Although only one enantiomer is shown, it will be understood that the formula IV is used herein to designate the transconfiguration of the 3-and 4-phenyl groups and that both the d- and l-enantiomers, as well as the racemic mixture, are included.

3,4-diarylchromans are prepared according to known methods, such as those disclosed in U.S. Pat. No. 3,340,276 to Carney et al., U.S. Pat. No. 3,822,287 to Bolger, and Ray et al., J Med Chem 19 (1976), 276–279, the contents of which are incorporated herein by reference. Conversion of the cis isomer to the trans configuration by means of an organometallic base-catalyzed rearrangement is disclosed in U.S. Pat. No. 3,822,287. The optically active d- and l-enantiomers may be prepared as disclosed by Salman et al.

in U.S. Pat. No. 4,447,622 (incorporated herein by reference) by forming an optically active acid salt which is subjected to alkaline hydrolysis to produce the desired enantiomer. If R2 is different from R3 and R4 is different from R5, the general formula I covers 8 optical isomers.

Within the present invention, 3,4-diarylchromans of formula I may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent. 3,4-diarylchromans of formula I and their salts are useful within human and veterinary medicine, for example, in the treatment of patients suffering from benign prostatic hypertrophy. For use within the present invention, 3,4-diarylchromans of formula I and their pharmaceutically acceptable salts are formulated with a pharmaceutically acceptable carrier to provide a medicament for parenteral, oral, nasal, rectal, subdermal or intradermal or transdermal administration according to conventional methods. Formulations may further include one or more diluents, fillers, emulsifiers, preservatives, buffers, excipients, etc, and may be provided in such forms as liquids, powders, emulsions, suppositories, liposomes, transdermal patches, controlled release, derreal implants, tablets, etc. One skilled in this art may formulate the compounds of formula I in an appropriate manner, and in accordance with accepted practices, such as those disclosed in *Remington's Pharmaceutical Sciences*, Gennaro, ed., Mack Publishing Co., Easton, Pa, 1990.

Oral administration is preferred. Thus, the active compound of formula I is prepared in a form suitable for oral administration, such as a tablet or capsule. Typically, a pharmaceutically acceptable salt of the compound of formula I is combined with a carrier and moulded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions containing a compound of formula I may be administered one or more times per day or week. An effective amount of such a pharmaceutical composition is the amount that provides a clinically significant effect against benign prostatic hypertrophy. Such amounts will depend, in part, on the particular condition to be treated, age, weight, and general health of the patient, and other factors evident to those skilled in the art. A typical daily dose will contain a nontoxic dosage range of from about 0.001 to about 75 mg/kg patient per day of a compound of the present invention, preferably in a range from about 0.01 to 75, more preferably in the range from about 0.01 to 50, and especially in the range from about 0.1 to 25, mg/kg patient per day.

The pharmaceutical compositions containing a compound of formula I may be administered in unit dosage form one or more times per day or week. In the alternative, they may be provided as controlled release formulations suitable for dermal implantation. Implants are formulated to provide release of active compound over the desired period of time, which can be up to several years. Controlled-release formulations are disclosed by, for example, Sanders et al., *J Pharm Sci* 73 (1964), 1294–1297, 1984; U.S. Pat. No. 4,489,056; and U.S. Pat. No. 4,210,644, which are incorporated herein by reference.

The following examples are offered by way of illustration, not limitation.

Examples of preferred compounds of formula I are centchroman as a racemic mixture and as isolated l-centchroman and d-centchroman enantiomers. Furthermore, 3,4-trans-2,2-dimethyl-3-phenyl-4-[4-(2-(pyrrolidin-1-yl)ethoxy)phenyl-7-hydroxychroman is a preferred compound. The more preferred compound is isolated l-centchroman (l-3,4-trans-2,2-dimethyl-3-phenyl-4-[4-(2-(pyrrolidin-1-yl)ethoxy)phenyl]-7-methoxychroman).

Examples of pharmaceutically acceptable acid addition salts are salts with non-toxic acids, either inorganic acids such as hydrochloric acid, sulphuric acid and phosphoric acid, or organic acids such as formic acid, fumaric acid, acetic acid, propionic acid, succinic acid, gluconic acid, lactic acid, citric acid, ascorbic acid, benzoic acid, embonic acid, methanesulphonic acid and malonic acid.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLE 1

Sixty sexually mature male Sprague-Dawley rats were assigned to one of the following five treatment groups (12 rats per group): 1)saline, 2) l-centchroman 0.025 mg/kg/day, 3) l-centchroman 0.125 mg/kg/day, 4) l-centchroman 0.625 mg/kg/day and 5)l-centchroman 3.125 mg/kg/day. The doses were administered three times per week for 13 weeks by oral gavage. At the conclusion of the experiment and autopsy was performed, the prostate gland and testes were isolated and weighed. L-centchroman had no effect on the average testis weight between the groups. However, a marked and dose-dependent effect on the prostate gland was observed as illustrated in Table 1.

TABLE 1

Effect of l-centchroman on prostate gland weight in Sprague-Dawley rats

| Treatment | Prostate gland (g) |
|---|---|
| Saline | 0.639 ± 0.239 |
| l-centchroman 0.025 mg/kg/day | 0.669 ± 0.149 |
| l-centchroman 0.125 mg/kg/day | 0.472 ± 0.126* |
| l-centchroman 0.625 mg/kg/day | 0.430 ± 0.122* |
| l-centchroman 3.125 mg/kg/day | 0.368 ± 0.124* |

Values are mean ± SD. *indicate significant reduction of prostate gland weight compared to saline treated rats.

We claim:

1. A method for treatment or prophylaxis of benign prostatic hypertrophy comprising administering to an adult male patient in need of such treatment or prophylaxis a compound of formula I

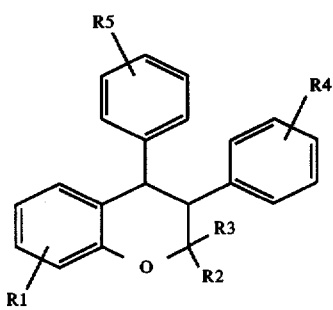

(I)

wherein R1, R4, and R5 are individually hydrogen, hydroxy, halogen, trifluoromethyl, lower alkyl, lower alkoxy or (tertiary amino) (lower alkoxy); and R2 and R3 are individually hydrogen or lower alkyl, or a pharmaceutically acceptable salt thereof in a range of from about 0.001–75 mg/kg patient per day.

2. The method according to claim 1 in which R1 is lower alkoxy.

3. The method according to claim 1 wherein R1 is methoxy.

4. The method according to claim 1 wherein R2 is methyl.

5. The method according to claim 1 wherein R3 is methyl.

6. The method according to claim 1 wherein R4 is hydrogen.

7. The method according to claim 1 wherein R5 is a group having formula II below:

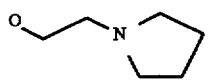

(II)

8. The method according to claim 1 wherein said compound has the formula III:

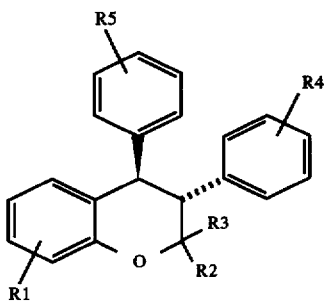

(III)

9. The method according to claim 1 wherein said compound is an isolated d- or l-enantiomer.

10. The method according to claim 1 wherein said compound is an isolated l-enantiomer.

11. The method according to claim 1 wherein said compound is 3,4-trans-2,2-dimethyl-3-phenyl-4-[4-(2-(pyrrolidin-1-yl)ethoxy)phenyl]-7-methoxychroman shown in formula IV below:

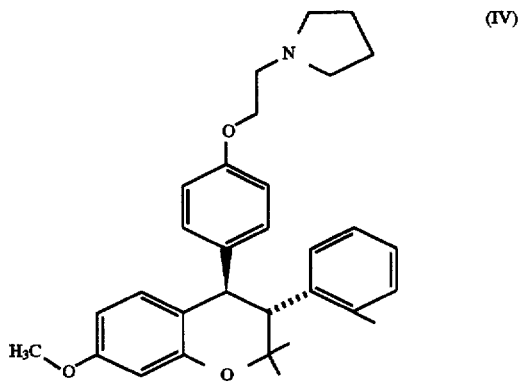

(IV)

12. The method according to claim 1 wherein said compound is an isolated d- or l-enantiomer of 3,4-trans-2,2-dimethyl-3-phenyl-4-[4-(2-(pyrrolidin-1-yl)ethoxy)phenyl]-7-methoxychroman.

13. The method according to claim 1 wherein said compound is l-3,4-trans-2,2-dimethyl-3-phenyl-4-[4-(2-(pyrrolidin-1-yl)ethoxy)phenyl]-7-methoxychroman.

14. The method according to claim 1 wherein said compound is administered orally.

15. The method according to claim 1 wherein said compound is administered in a range from about 0.01 to 75 mg/kg patient per day.

16. The method according to claim 1 wherein said compound is administered in a range from about 0.01 to 50 mg/kg patient per day.

17. The method according to claim 1 wherein said compound is administered one or more times per day or week.

18. The method according to claim 1 wherein said compound is administered in the form of a dermal implant.

* * * * *